:::

United States Patent [19]

Hara

[11] Patent Number: 5,646,014
[45] Date of Patent: Jul. 8, 1997

[54] PEPTIDE, ANTIBACTERIAL AGENT, PEPTIDE GENE, RECOMBINANT DNA AND METHOD FOR PREPARING THE PEPTIDE

[75] Inventor: Seiichi Hara, Noda, Japan

[73] Assignee: Agriculture, Forestry and Fisheries Technical Information Society, Japan

[21] Appl. No.: 520,599

[22] Filed: Aug. 29, 1995

[30] Foreign Application Priority Data

Aug. 31, 1994 [JP] Japan .................................. 6-207342
May 24, 1995 [JP] Japan .................................. 7-125440

[51] Int. Cl.$^6$ .......................... C12P 21/06; C07K 14/00; C07H 21/00
[52] U.S. Cl. .................... 435/69.1; 530/324; 536/22.1
[58] Field of Search ................. 435/69.1, 91.1, 435/240.2; 514/44; 530/324; 536/22.1, 23.1

[56] References Cited

PUBLICATIONS

Messing, J., "New M13 Vectors for Cloning," Methods in Enzymology 101:20–78.
Hohn, B., "In vitro Packaging of λ and Cosmid DNA," Methods in Enzymology 68:299–309.
Dagert, M., et al., "Prolonged Incubation of Calcium Chloride Improves the Competence of Escherichia coli Cells," Gene 6:23–28 (1979).
Steiner, H., et al., "Sequence and specificity of two antibacterial proteins involved in insect immunity," Nature 292:246–48 (Jul. 1981).
Peterson, G.L., "Determination of Total Protein," Methods in Enzymology 91:95–119.
Schägger, H., et al., "Tricine–Sodium Dodecyl Sulfate–Polyacrylamide Gel Electrophoresis for the Separation of Proteins in the Range from 1 to 100 kDA," Anal. Biochem. 166:368–79 (1987).
Casteels, P., et al., "Isolation and characterization of abaecin, a major antibacterial response peptide in the honeybee (Apis mellifera)," Eur. J. Biochem. 187:381–86 (1990).
Morishima, I., et al., "Isolation and Structure of Cecropins, Inducible Antibacterial Peptides, from the Silkworm Bombyx Mori," Comp. Biochem. Physiol. 95B:551–554 (1990).
Ikemura, T., "Correlation between the Abundance of Escherichia coli Transfer RNAs and the Occurrence of the Respective Codons in its Protein Genes: A Proposal for a Synonymous Codon Choice that is Optimal for the E. coli Translational System," J. Mol. Biol. 151:389–409 (1981).

Ikehara, M., et al., "Synthesis of a gene for human growth hormone and its expression in Escherichia coli," Proc. Natl. Acad. Sci. USA 81:5956–5960 (Oct. 1984).
Tu, Y.–Z., et al., "Purification, Characterization and Structure of $CM_2Ph_1$, An Antibacterial Peptide from Bombyx mori," Science in China (Series B) 32(9):1072–81 (Sep. 1989).
Morishima, I., et al., "Parallel Induction of Cecropin and Lysozyme in Larvae of the Silkworm, Bombyx mori," Dev. & Comp. Immunol. 19(5):357–63 (1995).
Boman, H.G., et al., "Cell–Free Imunity in Insects," Ann. Rev. Microbiol. 41:103–26 (1987).
Cociancich, S., et al., "The Inducible Antibacterial Peptides of Insects," Parasitology Today 10(4):132–39 (1994).
Powning, R. F., et al., "Studies on Insect Bacteriolytic Enzymes–I. Lysozyme in Haemolymph of Galleria mellonella and Bombyx mori," Comp. Biochem. Physiol. 45B:669–81 (1973).
Hultmark, D. Immune reactions in Drosophila and other insects: a model for innate immunity. trends in Genetics. vol. 9(5):178–183.
Hara and Yamakawa. Moricin, a novel type of antibacterial peptide isolated from the silkworm, Bombyx mori, J. Biol. Chem., vol. 270(50):29923–29927.
Theopold et. al.. Helix pomatia lectin, an inducer of Drosophila immnue response, Binds to hemomucin, a novel surface mucin. J. Biol. Chem.. vol. 271(22):12708–12715.

Primary Examiner—David Guzo
Assistant Examiner—William Sandals
Attorney, Agent, or Firm—Finnegan, Henderson, Farabow, Garrett & Dunner, L.L.P.

[57] ABSTRACT

The present invention relates to a peptide represented by the amino acid sequence of SEQ ID NO: 1, an antibacterial agent comprising the peptide as an active ingredient, a peptide gene encoding the peptide, a recombinant DNA comprising the peptide gene and a method for producing a peptide.

The peptide of the present invention exhibits an effective antibacterial activity against various Gram-negative and -positive bacteria including Staphylococcus aureus and Bacillus cereus which are pathogenic bacteria causing food poisoning. Therefore, this peptide is useful as a food preservative and an antibacterial agent for medical use.

14 Claims, No Drawings

PEPTIDE, ANTIBACTERIAL AGENT, PEPTIDE GENE, RECOMBINANT DNA AND METHOD FOR PREPARING THE PEPTIDE

BACKGROUND OF THE INVENTION

1. Field of the Invention

This invention relates to a novel peptide present in a silkworm hemolymph wherein an antibacterial activity has been induced, an antibacterial agent comprising the peptide as an active ingredient, a novel peptide gene encoding the peptide, a novel recombinant DNA comprising the gene and a method for preparing the novel peptide.

2. Description of the Prior Art

When bacteria invade the body cavity (coelom) of an insect, an antibacterial protein or peptide is induced in a hemolymph of the insect as one of biodefense reactions. As antibacterial proteins or peptide obtainable from a silkworm hemolymph, there are known lysozyme, cecropins and the like. Lysozyme, however, exhibits an antibacterial activity against only extremely limited Gram-positive bacteria such as Micrococcus. On the other hand, cecropins exhibit an antibacterial activity against various Gram-negative and -positive bacteria, but there is a problem that they do not exhibit an effective antibacterial activity against pathogenic bacteria causing food poisoning, such as *Staphylococcus aureus* and *Bacillus cereus*.

OBJECTS AND SUMMARY OF THE INVENTION

It is an object of the present invention to provide a novel peptide and an antibacterial agent comprising the peptide as an active ingredient. It is another object of the present invention to provide a method for efficiently producing the peptide by using genetic engineering techniques.

The present inventors have succeeded in isolating from an antibacterial acitivity-induced silkworm hemolymph a novel antibacterial peptide which exhibits an excellent antibacterial activity against *Escherichia coli, Staphylococcus aureus, Bacillus cereus* and the like. Furthermore, the present inventors have established a method for efficiently producing the novel peptide by using genetic engineering techniques. Thus, the present invention has been achieved.

The present invention provides:

(1) A novel peptide represented by (a) the amino acid sequence described in SEQ ID NO: 1 or (b) an amino acid sequence homologous to (a) which contains one or more additions, deletions or replacements of one or more amino acid residues within SEQ ID NO: 1 and exhibits an antibacterial activity.

(2) An antibacterial agent comprising the peptide of (1) as an active ingredient.

(3) A novel peptide gene encoding (a) the amino acid sequence described in SEQ ID NO: 1 or (b) an amino acid sequence homologous to (a) which contains one or more additions, deletions or replacements of one or more amino acid residues within SEQ ID NO: 1 and exhibits an antibacterial activity.

(4) A novel recombinant DNA which is obtained by inserting the peptide gene of (3) into a vector DNA.

(5) A method for producing a novel peptide, comprising culturing ina medium a bacterium which belongs to the genus Escherichia and comprises the recombinant DNA of (4) and recovering the peptide from the culture.

DETAILED DESCRIPTION OF THE INVENTION

The novel peptide of the present invention (hereinafter referred to as "moricin") can be prepared from, for example, an antibacterial activity-induced silkworm hemolymph by conventional methods for isolating a protein. Alternatively, moricin can be prepared by conventional peptide synthesizing techniques or genetic engineering techniques.

As to the genetic engineering techniques, there may be enumerated, for example, a method for producing a novel peptide by using a host cell which is transformed or transduced with a recombinant DNA wherein a novel peptide gene has been inserted and a method for producing moricin by translating the recombinant DNA in a cell-free protein synthesis system using rabbit reticulocytes, wheat embryos or the like.

Now, the method for isolating moricin from an antibacterial activity-induced silkworm hemolymph and the method for producing moricin using genetic engineering techniques will be described in detail.

[1] Method for Isolating Moricin from an Antibacterial Activity-Induced Silkworm Hemolymph With respect to the starting material for obtaining moricin, any silkworm hemolymph in which an antibacterial activity has been induced may be used. As to the method for inducing an antibacterial activity, for example, there may be used a method in which a suspension of *E. coli* in physiological saline is injected into the body cavity of a silkworm larva.

Eighteen to twenty-four hours after the induction of an antibacterial activity, legs of the silkworm larva are cut off to thereby collect a hemolymph. After heating, this hemolymph is centrifuged to obtain a supernatant.

Then, the thus obtained supernatant is subjected to salting out. As examples of the salts used for salting out, ammonium sulfate, sodium sulfate, magnesium sulfate and the like may be enumerated. These salts are added to the supernatant to give 15% to 75% saturation and the resultant precipitate is recovered.

Next, the precipitate is dissolved in distilled water, a buffer containing ammonium acetate, etc. and subjected to gel filtration. By this operation, the fractionation and desalting of proteins are achieved. The gel filtration media may be any media which is used in conventional gel filtration. For example, Sephadex G-50, G-75 and G-100 (Pharmacia Fine Chemical) and Toyopearl HW-55 (Tosoh Corp.) may be enumerated.

Then, low molecular mass protein fractions obtained by gel filtration are subjected to cation exchange column chromatography. As examples of the cation exchanger, CM Sepharose FF (Pharmacia Fine Chemical) and CM Toyopearl 650 (Tosoh Corp.) may be enumerated.

Out of the fractions adsorbed to the cation exchange column, the fraction which exhibits the strongest antibacterial activity is subjected to high performance liquid chromatography using a reversed-phase column (hereinafter referred to as "reversed-phase HPLC"). As examples of the reversed-phase column used here, Capcell Pak C8 SG300 and C18 SG300 (Shiseido Co., Ltd.) may be enumerated. The fractions adsorbed to the reversed-phase column can be eluted with density gradients of acetonitrile containing trifluoroacetic acid.

Out of the adsorbed fractions obtained, the fraction which exhibits the strongest antibacterial activity is re-subjected to reversed-phase HPLC to thereby isolate moricin.

The measurement of the antibacterial activity of the fraction obtained through the above-mentioned isolation and purification processes can be performed by using as an indicator the formation of a growth inhibition zone on an agar plate and using, for example, *Staphylococcus aureus* subsp. *aureus* ATCC 6538P as a test bacterium.

[2] Method for Producing Moricin Using Genetic Engineering Techniques

Hereinbelow, there will be described a method for producing moricin, comprising transforming or transducing a host cell with a recombinant DNA wherein a moricin gene-containing DNA has been inserted and producing moricin by using the recombinant microorganism obtained.

A moricin gene-containing DNA can be obtained by cloning a natural moricin gene derived from the silkworm genome DNA or cDNA. This moricin gene-containing DNA may be amplified by synthesizing a set of primer DNAs based on the amino acid sequence of moricin and then subjecting them to PCR. It is also possible to construct a moricin gene-containing DNA by chemical synthesis.

It should be noted that the amino acid sequence encoded by a moricin gene may contain one or more additions, deletions or replacements of one or more amino acid residues, as long as the amino acid sequence retains an antibacterial activity. All of the moricin genes in which the amino acid sequences have been altered within such an extent that does not eliminate the antibacterial activity are included in the scope of the present invention.

It is preferred that each end of a moricin gene-containing DNA be provided with a recognition site for a suitable restriction enzyme, such as EcoRI or SalI. When the DNA has such recognition sites, the insertion of this DNA into a vector DNA can be performed efficiently.

When a moricin gene-containing DNA is chemically sythesized, the DNA are synthesized as a plurality of oligonucleotides. After annealing, the oligonucleotides are ligated with DNA ligase. In this case, it is preferred that codons be replaced with those which would not influence the amino acid sequence of moricin and at the same time which are frequently used in a host cell to be employed. By the above procedures, it becomes possible to produce a larger quantity of moricin protein compared to the production using a natural moricin gene.

A moricin gene-containing DNA can be easily amplified by the method described below. In brief, the DNA is inserted into an appropriate vector DNA, e.g., a plasmid DNA or a bacteriophage DNA, to thereby obtain a recombinant DNA. Then, a host cell such as *Escherichia coli* JM109 (Takara Shuzo Co., Ltd.) is transformed or transduced by using the recombinant DNA to thereby obtain a recombinant microorganism. The thus obtained recombinant microorganism is cultured. After the recombinant DNA has been prepared by conventional methods, the insert DNA is cut out by using appropriate restriction enzymes. Then, the insert DNA obtained is purified. Incidentally, when a recombinant DNA is prepared from a recombinant microorganism, it is preferred that the base sequence of the insert DNA be confirmed by the dideoxy chain termination method [Methods Enzymol., 101:20–78 (1983)] or the like.

With respect to the host cell for producing moricin, either an eucaryotic cell or a procaryotic cell may be used. Examples of eucaryotic cells include cells of animals, plants, insects and yeasts, and examples of procaryotic cells *E. coli, Bacillus subtilis* and Actinomycetes.

When a plant cell or an insect cell is used as a host cell, such a cell need not be a cultured cell; a plant body or an insect body, for example, a tobacoo plant or a silkworm larva may be used as a host cell.

In the case of producing an antibacterial peptide such as moricin in a procaryotic cell such as *E. coli*, it is preferred that the peptide of interest be expressed as a fusion protein with β-galactosidase, β-lactamase, maltose-binding protein, protein A or the like. Since a moricin peptide which is expressed as does not exhibit an antibacterial activity, it does not inhibit the proliferation of the procaryotic host cell. As concrete examples of the procaryotic cell which can be used as a host in the present invention, *Escherichia coli* JM109, *Escherichia coli* HB101 (ATCC33694) and the like may be enumerated.

An antibacterial peptide expressed as a fusion protein can be easily purified by affinity chromatography when the fusion protein is soluble or by centrifugation when the fusion protein is insoluble.

With respect to the vector DNA for expressing a moricin peptide, any vector DNA may be used, as long as the vector DNA is capable of replication in a host cell. For example, a plasmid DNA and a bacteriophage DNA may be used. When the host cell is *E. coli*, plasmids such as pMAL-C2 (New England Labs. ), pGEX-5X-1 (Pharmacia) and pXa1 (Boehringer Mannheim) may be used.

Then, a moricin gene-containing DNA is inserted between appropriate restriction enzyme sites of a vector DNA to thereby prepare a recombinant DNA. When plasmid pXa1 is used as a vector DNA, the plasmid is digested by restriction enzymes such as EcoRI and SalI to therebyby obtain vector DNA fragments. Next, a moricin gene-containing DNA is mixed with the vector DNA fragments. A DNA ligase such as T4 DNA ligase is reacted with the resultant mixture to thereby obtain a recombinant DNA.

A recombinant microorganism can be obtained by transfoming or transducing a host cell with the above-mentioned recombinant DNA. The transformation of a host cell may be performed by D. M. Morrison's method [Methods Enzymol., 68:326–331 (1979)], the calcium chloride method [Gene, 6:23 (1979)] or the like, and the transduction of a host cell by B. Hohn's method [Methods Enzymol., 68:299–309 (1979)] or the like.

Next, the recombinant microorganism obtained is cultured in a medium and moricin is recovered from the culture.

When moricin is expressed not as a fusion protein but as a moricin peptide itself by using an eucaryotic cell as a host cell, the moricin peptide can be recovered by using conventional methods for protein isolation. In brief, cells are disrupted by lysis treatment using a detergent, sonication, milling treatment or the like to thereby discharge the moricin peptide from the cells. Then, by using similar methods as used for isolating moricin from a silkworm hemolymph (i.e., gel filtration, ion exchange and reversed-phase HPLC), a highly purified moricin standard product can be obtained.

When moricin is expressed as a fusion protein by using an eucaryotic or procaryotic cell as a host cell, the fusion protein is obtained by a combination of treatments such as centrifugation and affinity chromatography following cell breakage. Then, a moricin peptide is cut out from the fusion protein by a chemical treatment with cyanogen bromide or the like or by an enzyme treatment with Factor Xa (Boehringer Mannheim) or the like. The moricin peptide obtained is then purified.

A moricin peptide obtained by genetic engineering techniques exhibits a completely identical antibacterial activity with the one exhibited by a moricin peptide which is isolated from an antibacterial activity-induced silkworm hemolymph.

Moricin is able to exhibit an antibacterial activity against wide variety of bacteria including *Bacillus subtilis* which makes cooked rice, bread, etc. rotten; *Staphylococcus aureus* which is a pathogenic bacterium causing food poisoning; *Escherichia coli*; and other Gram-positive bacteria belonging to the genera Bacillus, Staphylococcus, Clostridium, Streptococcus and the like and Gram-negative bacteria belonging to the genera Escherichia, Pseudomonas and the like.

Moricin can be used as an antibacterial agent as it is or after being formulated into a tablet, dust, wettable powder, emulsion, capsule or the like using a conventional solid carrier, liquid carrier, emulsion dispersant and the like. As to the carrier, water, gelatin, starch, magnesium stearate, lactose, gum arabic, vegetable oil, and the like may be enumerated.

The above-mentioned antibacterial agent include a food preservative, an antibacterial agent for medical use, a preservative for construction materials and/or paints, an antibacterial agent for horticultural use, a preservative for livestock feed, a preservative for fish feed and the like; the antibacterial agent can be used in a wide variety of fields.

When moricin is added to a food as a food preservative, moricin may be, for example, mixed in the food or coated on the food. The amount of moricin added in this case is 2 mg or more per kg of food, preferably 5–50 mg/kg.

Examples of foods to which moricin is applicable include processed marine products such as boiled fish paste; processed livestock products such as ham and sausage; beverages such as soft drinks and fruit juices; and confectionery such as cakes, puddings and buns with a bean-jam filling.

The antibacterial agent comprising moricin as an active ingredient may be suitably mixed with other bacteriocides, pharmaceutical products, antiseptic, food additives or the like and used in combination.

EFFECT OF THE INVENTION

Moricin exhibits an effective antibacterial activity against various Gram-negative and -positive bacteria including *Staphylococcus aureus* and *Bacillus cereus* which are pathogenic bacteria causing food poisoning. Therefore, moricin is useful as a food preservative and an antibacterial agent for medical purposes.

PREFERRED EMBODIMENTS OF THE INVENTION

Now the present invention will be described in more detail with reference to the following Example where moricin is isolated from an antibacterial activity-induced silkworm hemolymph; another Example where moricin is produced using genetic engineering techniques; and Test Examples for antibacterial activity. These Examples should not be construed as limiting the scope of the present invention.

Example 1

(1) Isolation of Moricin from an Antibacterial Activity-Induced Silkworm Hemolymph (i) A suspension of *Escherichia coli* HB101 ATCC33694 in physiological saline ($4 \times 10^8$ cells/ml) was injected into the body cavity of 700 silkworm larvae of fifth instar (variety: Bombyx mori var. Tokai x Asahi; obtained from the National Institute of Sericultural and Entomological Science, Ministry of Agriculture, Forestry and Fisheries) at a rate of 0.005 ml/larva to thereby induce an antibacterial activity. Twenty hours after the injection, the legs of the silkworm larvae were cut off and the hemolymph thereof were collected. Immediately after the collection, the hemolymph was heated on a hot water bath at 100° C. for 5 minutes and then centrifuged.

(ii) To 200 ml of the resultant supernatant, ammonium sulfate was added to give 15% saturation and the resultant precipitate was separated by centrifugation. To the resultant supernatant, ammonium sulfate was added to give 75% saturation. The precipitate was separated by centrifugation and then collected. The precipitate obtained was dissolved in 40 ml of distilled water.

(iii) The resultant solution was poured into a Sephadex G-50 column (5×100 cm) equilibrated with 50 mM ammonium acetate (pH 5.0) to thereby carry out gel filtration, and then the low molecular mass protein fractions were recovered.

(iv) The low molecular mass protein fractions were poured into a CM Sepharose FF column (2.5×4.4 cm) equilibrated with 50 mM ammonium acetate (pH 5.0). The adsorbed fractions were eluted by pouring into this column mixtures of 50 mM ammonium acetate (pH 5.0) and 0.8 mM ammonium acetate (pH 7.0) at 9.5:0.5, 9:1, 8:2, 7:3, 6:4, 5:5, 4:6 and 3:7 volume ratios by 50 ml one by one. The eluate was collected by 50 ml depending on the salt concentration. The fraction eluted with the 4:6 ratio mixture exhibited the strongest antibacterial activity.

(v) 10 ml of the fraction eluted with the 4:6 ratio mixture was subjected to reversed-phase HPLC (column: Capcell PaK C8 SG300 10×250 mm). The adsorbed fractions were eluted with density gradients of acetonitrile containing 0.1% trifluoloacetic acid. The remaining eluates were similarly subjected to reversed-phase HPLC and the fractions exhibiting the strongest antibacterial activity were collected.

(vi) The collected fractions were subjected to reversed-phase HPLC (column: Capcell PaK C8 SG300 4.6×250 mm) again for further purification. The adsorbed fractions were eluted with density gradients of acetonitrile containing 0.1% trifluoloacetic acid. The eluate was collected and the fraction exhibiting the strongest antibacterial activity was pooled. A portion of the pool was subjected to Tricine SDS polyacrylamide gel electrophoresis (hereinafter referred to as "Tricine SDS-PAGE") and the gel after running was stained with Coomassie Brilliant Blue R-250 (BRL). As a result, a single stained band was obtained.

(vii) By the above-mentioned procedures, 150 μg of moricin was obtained from 200 ml of the centrifuge supernatant of the silkworm hemolymph.

Incidentally, at the time of isolation of moricin, the measurement of its antibacterial activity was performed by using, as an indicator, the formation of a growth inhibition zone on an agar plate [Nature, 292:246 (1981)] and, as a test bacterium, *Staphylococcus aureus* subsp. *aureus* ATCC 6538P.

The quantity of the protein was measured according to the improved Lowry method [Methods Enzymol. 91:95 (1983)] and Tricine SDS-PAGE was performed according to the method described in Anal. Biochem. 166:368 (1987).

(2) Structural Analysis (a) Amino Acid Composition

The moricin obtained was hydrolyzed in 6N HCl containing 0.1% phenol (under reduced pressure, at 110° C., for 24 hours) and then analyzed in a Hitachi amino acid analyzer Model 835. The results are shown below.

| Amino acid | No. of moles/mol moricin |
|---|---|
| Lys | 8.8 |
| Ala | 5.9 |
| Ile | 4.8 |
| Asp + Asn | 4.0 |
| Gly | 3.1 |
| Val | 3.2 |
| Arg | 1.7 |
| Leu | 2.1 |
| Phe | 2.3 |
| Pro | 1.9 |
| Thr | 1.9 |
| His | 1.4 |
| Ser | 1.0 |

(b) Molecular Mass

The molecular mass of the moricin obtained was found to be 4543.1±0.6 Da as a result of analysis with a Perkin Elmer mass spectrometer Model API-III (Perkin Elmer Sciex).

(c) N-Terminal Amino Acid Sequence

The N terminal amino acid sequence of the moricin was analyzed by Edman degradation method using a protein sequencer Model 473A (Applied Biosystems). As a result, the amino acid sequence described in SEQ ID NO: 2 was obtained.

(d) Amino Acid Sequences of the Peptide Fragments from Endo-proteinase Digestion The moricin was digested by endoproteinase Asp-N (Takara Shuzo) and the resultant peptide fragments were isolated by reversed-phase HPLC. The amino acid sequence of each of the fragments was analyzed by Edman degradation method. As a result, the amino acid sequences shown in SEQ ID NOS: 3 and 4 were obtained.

(e) From the results of the amino acid analysis, the mass analysis and the amino acid sequence analysis, it was concluded that the moricin obtained is a peptide having the amino acid sequence described in SEQ ID NO: 1.

Test Example 1

Antibacterial Activity Test (1)

In order to examine the antibacterial activity of the moricin obtained in Example 1 against various bacteria, the minimum inhibitory concentration (M.I.C.) of moricin was measured based on the method described in Eur. J. Biochem., 187:381–386 (1990). The results obtained are shown in Table 1.

(Test Bacteria)

*Escherichia coli* JM109 (Takara Shuzo)
*Staphylococcus aureus* subsp. *aureus* ATCC 6538P
*Bacillus cereus* IF03457

(Test Media)

When *E. coli* and *Staphylococcus aureus* subsp. *aureus* were used as test bacteria, brain heart infusion medium (BHI medium, Difco) was used. When *Bacillus cereus* was used as a test bacterium, nutrient broth medium (NB medium, Difco) was used.

(Method for Testing the Antibacterial Activity)

To a test medium suspending a test bacterium at a concentration of $4 \times 10^4$ cells/ml, an equal volume of the same medium containing moricin at varied concentrations was added and incubated at 30° C. for 20 hours. After the incubation, an equal volume of 6% formalin was added thereto to give a two-fold dilution. Then, the degree of cell proliferation was examined by measuring the absorbance at 650 nm. As a control, cecropin B1 [Comp. Biochem. Physiol. 95B:551 (1990)] was used which is a known antibacterial peptide derived from silkworm.

TABLE 1

| | Test | M.I.C. (μg/ml) | |
|---|---|---|---|
| Test Bacterium | Medium | Moricin | Cecropin B1 |
| *Escherichia coli* JM109 | BHI | 8 | <1 |
| *Staphylococcus aureus* subsp. *aureus* ATCC 6538P | BHI | 2 | >16 |
| *Bacillus cereus* IF03457 | NB | 8 | >16 |

Test Example 2

Antibacterial Activity Test (2)

The antibacterial activity of the moricin obtained in Example 1 against various bacteria was examined based on the method described in Nature, 292:246 (1981). The results obtained are shown in Table 2.

(Test Bacteria)

*Escherichia coli* JM109 (Takara Shuzo)
*Pseudomonas fluorescens* IAM1179
*Bacillus subtilis* IAM1107
*Bacillus megaterium* IAM1030
*Bacillus cereus* IF03457
*Staphylococcus aureus* ATCC6538P
*Staphylococcus aureus* IF03083
*Staphylococcus epidermis* IF012993
*Staphylococcus xylosus* IAM1312
*Pseudomonas aeruginosa* IAM1514
*Streptococcus pyogenes* ATCC21547

(Test Media)

NB plate medium containing 0.8% agarose (optionally, sodium chloride was added thereto to give a concentration of 150 mM) was used.

When *Streptococcus pyogenes* was used as a test bacterium, 0.8% agarose-containing BHI plate medium was used.

(Method for Testing the Antibacterial Activity)

50 μM moricin solution was prepared. 2 μl of this solution was added to each well of a plate medium into which a test bacterium had been inoculated. The plate was incubated at 30° C. overnight and then diameters of the growth inhibition zones formed were measured. As a control, cecropin B1 was used. Incidentally, the diameter of the well was 2.0 mm. When the diameter of the inhibition zone is expressed as 2.0 mm in Table 2, it indicates that an inhibition zone was not formed.

TABLE 2

| | | Diameter of the Inhibition Zone (mm) | |
|---|---|---|---|
| | Addition of | | |
| Test Bacterium | Sodium Chloride | Moricin | Cecropin B1 |
| *Escherichia coli* JM109 | – | 8.7 | 10.1 |
| *Pseudomonas fluorescens* IAM1179 | – | 8.6 | 8.9 |
| *Pseudomonas aeruginosa* IAM1514 | – | 7.0 | 7.9 |

TABLE 2-continued

|  | Addition of Sodium Chloride | Diameter of the Inhibition Zone (mm) | |
|---|---|---|---|
| Test Bacterium |  | Moricin | Cecropin B1 |
| Bacillus subtilis IAM1107 | − | 9.7 | 7.8 |
| Bacillus megaterium IAM1030 | − | 11.3 | 10.9 |
| Bacillus cereus IFO3457 | − | 8.0 | 2.0 |
| Staphylococcus aureus ATCC6538P | − | 10.0 | 6.9 |
| Staphylococcus aureus ATCC6538P | + | 11.8 | 2.3 |
| Staphylococcus aureus IFO3083 | − | 9.0 | 2.0 |
| Staphylococcus epidermidis IFO12993 | − | 10.7 | 9.0 |
| Staphylococcus xylosus IAM1312 | − | 9.6 | 2.0 |
| Streptococcus pyogenes ATCC21547 | − | 11.0 | 2.0 |

As shown in Tables 1 and 2, moricin was found to exhibit a strong antibacterial activity against various Gram-negative and -positive bacteria including *Staphylococcus aureus* and *Bacillus cereus* which are pathogenic bacteria causing food poisoning.

Example 2

Production of Moricin by Genetic Engineering Techniques

The production of moricin by genetic engineering techniques was carried out according to the following procedures. In brief, a moricin gene-containing DNA was constructed by chemical synthesis. Then, plasmid pUCMOR1 was prepared by inserting into a plasmid the above-mentioned DNA. *E. coli* was transformed with pUCMOR1 to thereby amplify this plasmid. Next, plasmid pXAMOR1 for moricin expression was prepared by subcloning the insert DNA of pUCMOR1. Then, *E. coli* was transformed with this plasmid. Using the resultant recombinant microorganism, a moricin fusion protein was produced. The fusion protein was then treated with cyanogen bromide and roughly purified to obtain a roughly purified moricin.

Each of the above processes will be described more specifically below.

1. Construction of a Moricin Gene-Containing DNA by Chemical Synthesis (1) Determination of the Base Sequence The DNA sequence to be constructed (i.e., a moricin gene-containing DNA) was determined by utilizing those codons which are frequently used in *E. coli* [Ikemura, T., J. Mol. Biol., 151:389–409 (1987)]. The structure of this DNA is as follows: at the downstream of the Eco RI recognition site, there are a codon corresponding to methionine (ATG) for the purpose of cutting out with cyanogen bromide, a moricin gene, two termination codons (TAA and TAG), and the SalI recognition site positioned in this order. The base sequence of the moricin gene determined is shown in SEQ ID NO: 5.

(2) Chemical Synthesis of Oligonucleotides

The moricin gene-containing DNA were divided into 8 oligonucleotides (mosy1–8) and each of them was chemically synthesized. The synthesis of these nucleotides was performed with a DNA synthesizer (ABI Model 392, Applied Biosystems) usinhg the phosphoamidite method.

The base sequences of mosy1–8 were as follows:

mosy1 AATTCATGGCTAAAATCCCGATTAAG-GCAATTAAA SEQ ID NO: 6
mosy2 ACTGTGGGCAAAGCTGTTGGTAAAG-GTCTGCGTG SEQ ID NO: 7
mosy3 CTATCAACATCGCTTCTACCGCTAAC-GACGTATTCAA SEQ ID NO: 8
mosy4 CTTCCTGAAACCGAAGAAACGTAAACAC-TAATAG SEQ ID NO: 9
mosy5 CACAGTTTTAATTGCCTTAATCGG-GATTTTAGCCATG SEQ ID NO: 10
mosy6 GTTGATAGCACGCAGACCTTTACCAA-CAGCTTTGCC SEQ ID NO: 11
mosy7 CAGGAAGTTGAATACGTCGTTAGCGGTA-GAAGCGAT SEQ ID NO: 12
mosy8 TCGACTATTAGTGTTTACGTTTCTTCGGTTT SEQ ID NO: 13

(3) Purification of Synthetic Oligonucleotides

The synthetic oligonucleotides were purified using QIAGEN Plasmid Kit (Funakoshi). First, a portion of the oligonucleotide synthesized in (2) above was dissolved in MOPS solution [50 mM MOPS (pH 7.0), 0.1M NaCl] to give a 20 µg/ml oligonucleotide solution.

To a purification tip (QIAGEN-tip 20) equilibrated with 2 ml of an equilibration solution [50 mM MOPS (pH 7.0), 0.1M NaCl, 0.15% Triton X-100], 1 ml of the above-mentioned oligonucleotide solution was added for the adsorption of the oligonucleotide. Then, the tip was washed with 4 ml of MOPS solution. Afterwards, the elution, precipitation and washing of the oligonucleotide were carried out according to the protocol of the kit manufacturer. Each of the oligonucleotides thus obtained (6–13 µg) was dissolved in 15 µl of TE solution [10 mM Tris-HCl (pH 8.0), 1 mM EDTA].

(4) Phosphorylation of Oligonucleotides

The 5' ends of the six oligonucleotides from mosy2 to mosy7 were phosphorylated with ATP and T4 polynucleotide kinase. The reaction was carried out in a separate tube for each oligonucleotide. The reaction conditions were as follows. 3 µg of an oligonucleotide (dissolved in TE solution), 2 µl of 10× kination buffer [500 mM Tris-HCl (pH 7.6), 100 mM MgCl$_2$, 50 mM DTT, 1 mM spermidine-HCl, 1 mM EDTA; Nippon Gene Co., Ltd.], 2 µl of 10 mM ATP and 20 U of T4 polynucleotide kinase (Nippon Gene) were mixed and distilled water was added thereto to give a 20 µl solution. This solution was reacted at 37° C. for 2 hours. Then, the solution was heated at 90° C. for 3 minutes to terminate the reaction.

(5) Construction of the Moricin Gene-Containing DNA i. Annealing of Oligonucleotides The reaction solutions from the phosphorylation of each of mosy2–mosy7 were collected in one tube to obtain a 120 µl solution, to which 3 µg of mosy1 and 3 µg of mosy8 were added. To the resultant solution, 20 µl of 10× ligation buffer [500 mM Tris-HCl (pH 7.9), 100 mM MgCl$_2$, 200 mM DTT, 10 mM ATP; Nippon Gene] was further added. Then, distilled water was added thereto to give a 197 µl solution. This solution was heated at 90° C. for 5 minutes, then immediately cooled with ice and heated at 75° C. for 10 minutes in a heat block (Dry Thermo Unit Model AL-10; Taitec Co., Ltd.). Then, the heat bock was turned off and the solution was left for 5 hours.

ii. Ligation of Oligonucleotides

To 197 µl of the above reaction solution, 1800 U of T4 DNA ligase (Nippon Gene) was added and reacted at 16° C. for 14 hours.

iii. Purification of DNA

To a portion (30 µl) of the above reaction solution, 3 µl of BPB solution (0.1% BPB, 30% Glycerol) was added and subjected to 3% agarose gel electrophoresis, to thereby cut out a band about 140 bp in length. The DNA in the gel was recovered by freezing–thawing treatment and ethanol precipitation treatment. The obtained DNA (800 ng) was dissolved in 9 μl of 1× kination buffer.

iv. Phosphorylation of the Moricin Gene-Containing DNA

To 8 μl of the DNA solution obtained above, 1 μl of 10 mM ATP and 10 U of T4 polynucleotide kinase were added and reacted at 37° C. for 2 hours. Then, the solution was heated at 90° C. for 3 minutes to terminate the reaction.

2. Preparation of a Recombinant DNA (plasmid pUCMOR1)

Plasmid pUCMOR1 carries the moricin gene-containing DNA inserted thereinto. This plasmid was prepared as described below.

To a mixture of 4 μg of plasmid pUC119 (Takara Shuzo), 4 μl of 10× H buffer [500 mM Tris-HCl (pH 7.5), 100 mM MgCl$_2$, 10 mM DTT, 1000 mM NaCl; Takara Shuzo] and 20 U for each of restriction enzymes EcoRI (GIBCO BRL) and SalI (Takara Shuzo), distilled water was added to give a 40 μl solution. This solution was digested at 37° C. for 20 hours. Then, the solution was heated at 65° C. for 15 minutes to terminate the reaction. 2 μl of the resultant reaction solution (corresponding to 200 ng of the plasmid), 10 μl of the moricin gene DNA prepared in 1. (5) above, 2 μl of 10× ligation buffer, 2 μl of 2 μg/ml BSA and 1200 U of T4 DNA ligase were mixed and distilled water was added thereto to give a 20 μl solution. This solution was subjected to a ligation reaction at 16° C. for 6 hours.

20 μl of the above ligation reaction solution was mixed with 100 μl of a competent cell (*Escherichia coli* JM109, Nippon Gene) solution and then the cell was transformed while maintaining the mixed solution on ice for 30 minutes, at 37° C. for 2 minutes and on ice for 5 minutes. Next, 400 μl of High Competent Broth (Nippon Gene) was added to the solution and incubated at 37° C. for 1 hour with shaking. The resultant culture was spread evenly over 4 plates of 2×YT (1.6% Trypton, 1% yeast extract, 0.5% NaCl) agar medium containing 50 μg/ml ampicillin, 0.1 mM IPTG and 40 μg/ml X-gal and incubated at 37° C. for 20 hours, to thereby obtain about 300 ampicillin-resistant strains.

Out of these ampicillin-resistant strains, 20 strains forming light blue colonies were selected and incubated in 3 ml of LB liquid medium containing 50 μg/ml ampicillin at 37° C. for 10 hours.

The culture solution was centrifuged to harvest cells. Then, the plasmid DNA was purified using QIAGEN Plasmid Mini Kit (Funakoshi) and dissolved in 20 μl of TE solution.

To a mixture of 2 μl of the resultant plasmid solution, 1 μl of 10× H buffer, 3 U of EcoRI and 3 U of SalI, distilled water was added to give a 10 μl solution. This solution was reacted at 37° C. for 90 minutes.

To this reaction solution, 1 μl of BPB solution was added and subjected to 4% agarose gel electrophoresis, to thereby confirm the length of the insert DNA cut out by the restriction enzymes. Fragments of varied lengths from about 120 to 140 bp were observed.

With respect to 14 plasmids carrying an insert DNA of about 140 bp, the base sequence of each insert DNA was determined. This determination was carried out using Taq Dye Primer Cycle Sequencing Kit (ABI), GeneAmp PCR System 9600 (Perkin Elmer Cetus) and an ABI Model 373A DNA sequencer. There were 4 plasmids into which the moricin gene-containing DNA had been inserted. One of these plasmids was designated as pUCMOR1.

3. Preparation of a Recombinant DNA for Moricin Expression (Plasmid pXAMOR1)

Plasmid pXAMOR1 was obtained by subcloning the moricin gene-containing DNA inserted into plasmid pUCMOR1, between the EcoRI site and SalI site of plasmid pXa1. Plasmid pXAMOR1 is controled by lac promoter/operator and expresses a fusion protein comprising β-galactosidase, a collagen fragment and moricin. Details of the preparation of plasmid pXAMOR1 are as described below.

To a mixture of 5 μg of plasmid pXa1 (Boehringer Mannheim), 10 μl of 10× H buffer, 20 U of EcoRI and 20 U of SalI, distilled water was added to give a 100 μl solution. This solution was digested at 37° C. for 20 hours. Then, the solution was heated at 65° C. for 15 minutes to terminate the reaction. As a result, fragments of plasmid pXa1 were obtained.

On the other hand, plasmid pUCMOR1 was digested with EcoRI and SalI to thereby cut out the insert DNA, which was then purified by agarose gel electrophoresis. The reaction conditions were as follows.

To a mixture of 10 μg of plasmid pUCMOR1, 5 μl of 10× H buffer and 20 U for each of restriction enzymes EcoRI and SalI, distilled water was added to give a 50 μl solution. This solution was digested at 37° C. for 20 hours. To the resultant reaction solution, 3 μl of BPB solution was added and subjected to 3% agarose gel electrophoresis, to thereby cut out a band about 140 bp in length. Then, the DNA in the gel was recovered by freezing–thawing treatment and ethanol precipitation treatment. The obtained DNA (60 ng) was dissolved in 18 μl of distilled water.

Then, 20 ng of the purified insert DNA, 1 μl (50 ng) of plasmid pXa1 fragments, 1 μl of 10× ligation buffer, 1 μl of 2 μg/ml BSA and 600 U of T4 DNA ligase were mixed and distilled water was added thereto to give a 10 μl solution. This solution was subjected to a ligation reaction at 16° C. for 5 hours.

The above ligation reaction solution was mixed with 100 μl of a competent cell (*Escherichia coli* JM109, Nippon Gene) solution and then the cell was transformed while maintaining the mixed solution on ice for 30 minutes, at 37° C. for 2 minutes and on ice for 5 minutes. This reaction solution was spread over 2 plates of 2×YT agar medium containing 50 μg/ml ampicillin and incubated at 37° C. for 20 hours, to thereby obtain about 1000 ampicillin-resistant strains.

Out of these ampicillin-resistant strains, 10 strains were selected and incubated in 3 ml of LB liquid medium containing 50 μg/ml ampicillin at 37° C. for 10 hours. The culture solution was centrifuged to harvest cells. Then, the plasmid was purified using QIAGEN Plasmid Mini Kit and dissolved in 20 μl of TE solution.

To a mixture of 2 μl of the above plasmid solution, 1 μl of 10× H buffer, 3 U of EcoRI and 3 U of SalI, distilled water was added to give a 10 μl solution. This solution was reacted at 37° C. for 90 minutes. To this reaction solution, 1 μl of BPB solution was added and subjected to 4% agarose gel electrophoresis, to thereby confirm the length of the insert DNA cut out by the restriction enzymes. As a result, it was confirmed that every plasmid carried an insert DNA about 140 bp in length. One of these plasmids was designated as pXAMOR1. The recombinant *E. coli* containing pXAMOR1 was designated as (*E. coli*)JM109(pXAMOR1) and deposited at the National Institute of Bioscience and Human-technology, Agency of Industrial Science and Technology under the Accession No. FERM BP-5099.

4. Production of a Moricin Fusion Protein by the Recombinant Microorganism (1) Confirmation of the Production of a Fusion Protein One colony of the recombinant *E. coli* containing plasmid pXAMOR1, i.e., (*E. coli*)JM109(pXAMOR1) was inoculated into 2 ml of LB liquid medium and incubated at 37° C. for 2 hours. Then, 10 μl of 100 mM IPTG was added thereto to induce the expression of a fusion protein and the *E. coli* was further incubated at 37° C. for 2 hours. 0.5 ml of the culture solution was centrifuged to harvest cells. The cell pellet was suspended in 100 μl of a sample buffer [62.5 mM Tris-HCl (pH 6.8), 10% glycerol, 2% SDS, 5% 2-mercaptoethanol, 0.0025% BPB] and heated at 100° C. for 5 minutes. 3 μl of this suspension was subjected to SDS-PAGE. On the other hand, a culture solution of the recombinant *E. coli* incubated without the addition of IPTG was subjected to SDS-PAGE as a control.

The expected molecular mass of the fusion protein comprising β-galactosidase, a collagen fragment and moricin is 127.5 KDa. A band was observed at about 127.5 KDa only when the recombinant *E. coli* was cultured with the addition of IPTG; thus, the expression of the fusion protein was confirmed.

(2) Rough Purification of the Fusion Protein

The recombinant *E. coli* was incubated in 20 ml of 2×YT liquid medium containing ampicillin at 37° C. for 14 hours. Then, to 3 flasks individually containing 300 ml of 2×YT liquid medium containing 50 μg/ml ampicillin, the above-mentioned preculture solution was added (10 ml/flask) and incubated at 37° C. for 2 hours. Then, 1.5 ml of 100 mM IPTG was added to each flask and the *E. coli* was incubated for another 2 hours. The culture solution was centrifuged to harvest cells. As a result, 3.7 g of cells was obtained.

The cells were suspended in 35 ml of a suspension solution [20 mM Tris-HCl (pH 7.4), 200 mM NaCl, 1 mM EDTA (pH 8.0), 10 mM 2-mercaptoethanol]. This suspension was subjected to freezing-thawing and sonication (using Sonifier Cell Disrutor W200P; BRANSON) to disrupt the cells. Then, the resultant suspension of disrupted cells was centrifuged and the precipitate was suspended in 35 ml of a suspension solution [0.5% Triton X-100, 10 mM EDTA (pH 8.0)]. This suspension was recentrifuged. The supernatant was discarded to thereby obtain 9 mg of the protein. This material was subjected to the treatment with cyanogen bromide described below as a roughly purified fusion protein.

(3) Treatment with Cyanogen Bromide

To 1 mg of the roughly purified fusion protein obtained by the above-mentioned procedures, 200 μl of 70% formic acid and 10 μl of 100 mg/ml cyanogen bromide (dissolved in acetonitrile) were added and reacted at room temperature for 24 hours. Then, the reaction solution was dried under reduced pressure. The resultant material was subjected to the antibacterial activity test described below as a roughly purified moricin.

Test Example 3

Antibacterial Activity Test (3)

The antibacterial activity of the roughly purified moricin against various bacteria was examined based on the method described in Nature, 292:246 (1981). The results obtained are shown in Table 3.
(Test Bacteria)

*Staphylococcus aureus* ATCC6538P

*Streptococcus pyogenes* ATCC21547
*Escherichia coli* JM109 (Takara Shuzo)
*Pseudomonas fluorescens* IAM1179

(Test Media)

NB plate medium containing 0.8% agarose was used. (When *Staphylococcus aureus* was used as a test bacterium, sodium chloride was added to give a concentration of 150 mM.) When *Streptococcus pyogenes* was used as a test bacterium, BHI plate medium containing 0.8% agarose was used.

(Method for Testing Antibacterial Activity)

Distilled water was added to the roughly purified moricin to thereby prepare a protein suspension having a concentration of about 10 μg/μl. Two microliters of this suspension was applied to each well on a plate medium into which a test bacterium had been inoculated. Then, the plate was incubated at 30° C. overnight and the diameter of the growth inhibition zone formed was measured.

As controls, the following materials were prepared:

① A fusion protein (comprising β-galactosidase and a collagen fragment) which has been produced by the recombinant *E. coli* containing pXa1 and has not been treated with cyanogen bromide.

② The fusion protein which has been produced by the recombinant *E. coli* containing pXa1 and treated with cyanogen bromide.

③ The fusion protein (comprising β-galactosidase, a collagen fragment and moricin) which has been produced by the recombinant *E. coli* containing pXAMOR1 and has not been treated with cyanogen bromide.

When cyanogen bromide treatment was not carried out, 10 μl of acetonitrile was added instead of 10 μl of cyanogen bromide solution and a similar treatment was carried out.

TABLE 3

| | Diameter of the Inhibition Zone (mm) | | | |
|---|---|---|---|---|
| | Control ① | Control ② | Control ③ | Roughly purified moricin |
| *Staphylococcus aureus* ATCC6538P | 2 | 2 | 2 | 7.0 |
| *Streptococcus pyogenes* ATCC21547 | 2 | 2 | 2 | 5.3 |
| *Escherichia coli* JM109 | 2 | 2 | 2 | 5.9 |
| *Pseudomonas fluorescens* IAM1179 | 2 | 2 | 2 | 3.9 |

From the results shown in Table 3, it was found that, similar to a natural moricin isolated from a silkworm hemolymph, a moricin produced by a recombinant *E. coli* using genetic engineering techniques exhibits an antibacterial activity against Gram-positive and -negative bacteria.

In addition, moricin did not exhibit an antibacterial activity when it was in the form of a fusion protein; moricin exhibited an antibacterial activity only when it was separated from the fusion protein by the treatment with cyanogen bromide.

What is claimed is:

1. A peptide represented by (a) the amino acid sequence described in SEQ ID NO: 1 or (b) an amino acid sequence homologous to (a) which contains one or more additions, deletions or replacements of one or more amino acid residues within SEQ ID NO: 1 and exhibits an antibacterial activity.

2. An antibacterial agent comprising the peptide of claim 1 as an active ingredient.

3. A peptide gene encoding (a) the amino acid sequence described in SEQ ID NO: 1 or (b) an amino acid sequence homologous to (a) which contains one or more additions, deletions or replacements of one or more amino acid residues within SEQ ID NO: 1 and exhibits an antibacterial activity.

4. A recombinant DNA obtained by inserting the peptide gene of claim 3 into a vector DNA.

5. The recombinant DNA of claim 4, wherein the vector DNA is a plasmid DNA or a virus DNA.

6. The recombinant DNA of claim 5, wherein the vector DNA is pMAL-C2, pGEX-5X-1 or pXA1.

7. A host cell comprising the recombinant DNA of any one of claims 4 to 5.

8. The host cell of claim 7, wherein the host cell is a eucaryotic cell.

9. The host cell of claim 8, wherein the eucaryotic cell is selected from the group consisting of animal cell, a plant cell, an insect cell and a yeast cell.

10. A host cell comprising the recombinant DNA of any one of claims 4 to 6.

11. The host cell of claim 10, wherein the host cell is a procaryotic cell.

12. The host cell of claim 11, wherein the procaryotic cell is *Escherichia coli*.

13. The host cell of claim 12, wherein the host cell is *Escherichia coli* JM109.

14. A method for producing a peptide as described in SEQ ID NO: 1 comprising culturing the host cell selected from the group consisting of an animal cell, a plant cell, an insect cell a yeast cell, *Escherichia coli*, and *Escherichia coli* JM109 on a medium and recovering the peptide from the culture.

* * * * *

UNITED STATES PATENT AND TRADEMARK OFFICE
CERTIFICATE OF CORRECTION

PATENT NO. : 5,646,014
DATED : July 8, 1997
INVENTOR(S) : Seiichi HARA

It is certified that error appears in the above-indentified patent and that said Letters Patent is hereby corrected as shown below:

In claim 14, column 22, line 6, after "cell" (first occurrence) insert --,--.

In claim 14, line 7, change "*JM*" to --JM--.

Signed and Sealed this

Fifteenth Day of September, 1998

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
      ( A ) LENGTH: 42 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:1:

```
Ala  Lys  Ile  Pro  Ile  Lys  Ala  Ile  Lys  Thr  Val  Gly  Lys  Ala  Val  Gly
 1                    5                        10                       15

Lys  Gly  Leu  Arg  Ala  Ile  Asn  Ile  Ala  Ser  Thr  Ala  Asn  Asp  Val  Phe
               20                        25                       30

Asn  Phe  Leu  Lys  Pro  Lys  Lys  Arg  Lys  His
          35                        40
```

( 2 ) INFORMATION FOR SEQ ID NO:2:

( i ) SEQUENCE CHARACTERISTICS:
      ( A ) LENGTH: 33 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:2:

```
Ala  Lys  Ile  Pro  Ile  Lys  Ala  Ile  Lys  Thr  Val  Gly  Lys  Ala  Val  Gly
 1                    5                        10                       15

Lys  Gly  Leu  Arg  Ala  Ile  Asn  Ile  Ala  Ser  Thr  Ala  Asn  Asp  Val  Phe
               20                        25                       30

Asn
```

( 2 ) INFORMATION FOR SEQ ID NO:3:

( i ) SEQUENCE CHARACTERISTICS:
      ( A ) LENGTH: 29 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:3:

```
Ala  Lys  Ile  Pro  Ile  Lys  Ala  Ile  Lys  Thr  Val  Gly  Lys  Ala  Val  Gly
 1                    5                        10                       15

Lys  Gly  Leu  Arg  Ala  Ile  Asn  Ile  Ala  Ser  Thr  Ala  Asn
               20                        25
```

( 2 ) INFORMATION FOR SEQ ID NO:4:

( i ) SEQUENCE CHARACTERISTICS:
      ( A ) LENGTH: 13 amino acids
      ( B ) TYPE: amino acid
      ( C ) STRANDEDNESS: single
      ( D ) TOPOLOGY: linear ( i i ) MOLECULE TYPE: peptide (x i) SEQUENCE DESCRIPTION: SEQ ID NO:4:

```
Asp  Val  Phe  Asn  Phe  Leu  Lys  Pro  Lys  Lys  Arg  Lys  His
 1              5                        10
```

(2) INFORMATION FOR SEQ ID NO:5:

(i) SEQUENCE CHARACTERISTICS:
        (A) LENGTH: 126 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:5:

```
GCTAAAATCC CGATTAAGGC AATTAAAACT GTGGGCAAAG CTGTTGGTAA AGGTCTGCGT      60
GCTATCAACA TCGCTTCTAC CGCTAACGAC GTATTCAACT TCCTGAAACC GAAGAAACGT    120
AAACAC                                                                126
```

(2) INFORMATION FOR SEQ ID NO:6:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:6:

```
AATTCATGGC TAAAATCCCG ATTAAGGCAA TTAAA                                35
```

(2) INFORMATION FOR SEQ ID NO:7:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:7:

```
ACTGTGGGCA AAGCTGTTGG TAAAGGTCTG CGTG                                 34
```

(2) INFORMATION FOR SEQ ID NO:8:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:8:

```
CTATCAACAT CGCTTCTACC GCTAACGACG TATTCAA                              37
```

(2) INFORMATION FOR SEQ ID NO:9:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (i i) MOLECULE TYPE: DNA (genomic)

-continued ( x i ) SEQUENCE DESCRIPTION: SEQ ID NO:9:

CTTCCTGAAA CCGAAGAAAC GTAAACACTA ATAG  34

( 2 ) INFORMATION FOR SEQ ID NO:10:

( i ) SEQUENCE CHARACTERISTICS:
      ( A ) LENGTH: 37 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:10:

CACAGTTTTA ATTGCCTTAA TCGGGATTTT AGCCATG  37

( 2 ) INFORMATION FOR SEQ ID NO:11:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:11:

GTTGATAGCA CGCAGACCTT TACCAACAGC TTTGCC  36

( 2 ) INFORMATION FOR SEQ ID NO:12:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:12:

CAGGAAGTTG AATACGTCGT TAGCGGTAGA AGCGAT  36

( 2 ) INFORMATION FOR SEQ ID NO:13:

( i ) SEQUENCE CHARACTERISTICS:
      ( A ) LENGTH: 31 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:13:

TCGACTATTA GTGTTTACGT TTCTTCGGTT T  31